US00PP34561P2

(12) United States Plant Patent
Bourne

(10) Patent No.: US PP34,561 P2
(45) Date of Patent: Sep. 13, 2022

(54) GRAPEVINE NAMED 'SV34-150-338'

(50) Latin Name: ***Vitis vinifera* L.**
Varietal Denomination: SV34-150-338

(71) Applicant: Sunview Vineyards of California, Inc., Delano, CA (US)

(72) Inventor: Timothy F Bourne, Visalia, CA (US)

(73) Assignee: Sunview Vineyard of California, Inc., Delano, CA (US)

( * ) Notice: Subject to any disclaimer, the term of this patent is extended or adjusted under 35 U.S.C. 154(b) by 0 days.

(21) Appl. No.: 17/803,257

(22) Filed: Apr. 4, 2022

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 6/88; A01H 5/08
See application file for complete search history.

*Primary Examiner* — Keith O. Robinson
(74) *Attorney, Agent, or Firm* — Eric C. Cole; Baker Manock & Jensen, PC

(57) ABSTRACT

A new and distinct variety of grapevine plant named 'SV34-150-338' particularly characterized by its very large, crisp, sweet, yellow green berries which ripen in late mid-season in the McFarland, Calif. area.

3 Drawing Sheets

Scientific name of the genus and species of the plant claimed: The plant claimed relates to a new and distinct variety of *Vitis vinifera* L.

Variety denomination: The plant claimed shall be known as 'SV34-150-338'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* and hereinafter referred to as grapevine named 'SV34-150-338'. As used herein, 'grapevine' refers to all plant parts including, vines, canes, tendrils, leaves, fruit and roots of 'SV34-150-338'. Grapevine named 'SV34-150-338' is the result of an effort to produce a late ripening, green, seedless table grape with fruit characteristics superior to currently available green grape cultivar 'Autumn King' (U.S. Plant Pat. No. 16,284). This new cultivar originated from a cross conducted in May 2013 near McFarland, Calif. between female parent grapevine selection 'SV30-23-590' (unpatented) and male parent grapevine cultivar 'Princess' (unpatented). Resultant ovules from the cross were harvested 42 days after pollination and cultured on 'McCown's Woody Plant Medium'. Subsequently, the resultant embryonic plants were cultured in the same medium in the laboratory under twelve hours of light from standard fluorescent lamps at 29° C. The seedlings from this effort were transplanted to the greenhouse in November of 2013 and grown in the greenhouse at 29° C. with 12 hours illumination under high pressure sodium vapor lamps. This seedling population was planted in the field in the spring of 2014 near McFarland, Calif. The new grapevine was selected on Aug. 11, 2016. It was then propagated by cuttings and grafted to 'Freedom'

(unpatented) rootstock in 2017. The present invention has been found to retain its distinctive characteristics through two successive asexual propagations.

Grapevine named 'SV34-150-338' differs from the female parent grapevine 'SV30-23-590' (unpatented) in that 'SV34-150-338' has berries with small seed traces which are soft and not detectable when eaten while 'SV30-23-590' has large, partially lignified seed traces which are objectionable when eaten.

Grapevine named 'SV34-150-338' differs from its male parent 'Princess' (unpatented) in that 'SV34-150-338' has very large, elliptic berries that do not brown internally while in cold storage, whereas 'Princess' (unpatented) has oblong shaped, yellow berries and berries that brown internally while in cold storage.

Grapevine named 'SV34-150-338' differs from the commercial cultivar 'Sugrathirtyfive' (U.S. Plant Pat. No. 20,491) in that 'SV34-150-338' has fruit with a neutral, non-muscat flavor which 'Sugrathirtyfive' (U.S. Plant Pat. No. 20,491) has muscat flavor.

Grapevine named 'SV34-150-338' is most similar to its half sibling, grapevine named 'SV35-210-349' (plant patent applied for), from which it can be distinguished by its much larger clusters (1,190 g vs. 785 g).

SUMMARY OF THE INVENTION

The following are the most outstanding and distinguishing characteristics of this new variety when grown under normal horticultural practices near McFarland, Calif.:

1. Berries which are yellowish green in color;
2. Very firm berry texture; and
3. Very large, crisp berries with sweet taste.

BRIEF DESCRIPTION OF THE DRAWINGS

This new grapevine is illustrated by the accompanying photographs which show fruit clusters, leaves, canes, and tendrils of the seedling vine and plants propagated from it.

The colors shown are as true as can be reasonably obtained by conventional photographic procedures.

DETAILED BOTANICAL DESCRIPTION

Figure 1:
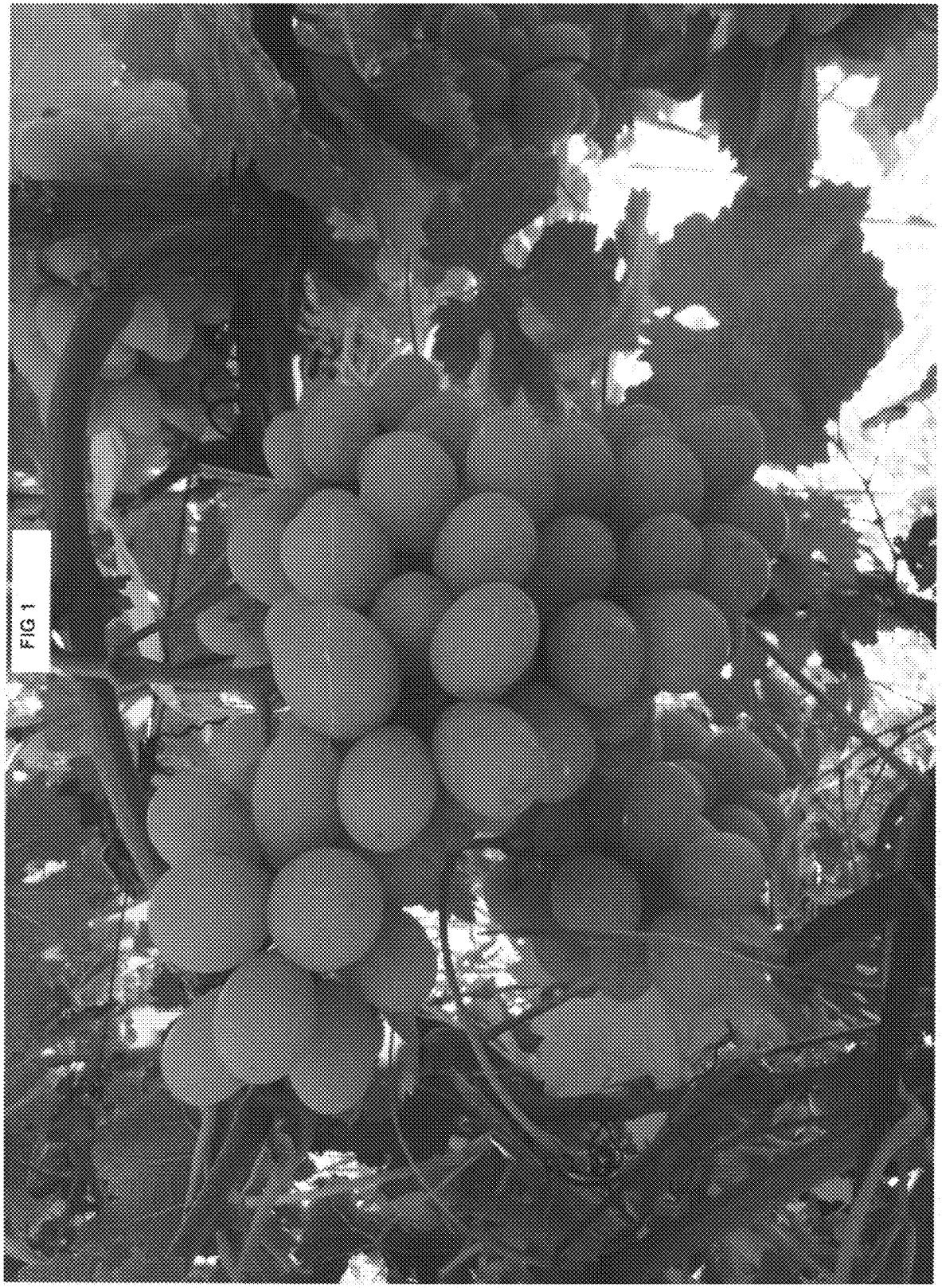
FIG. 1 Fruit cluster on the seedling vine.
Figure 2:
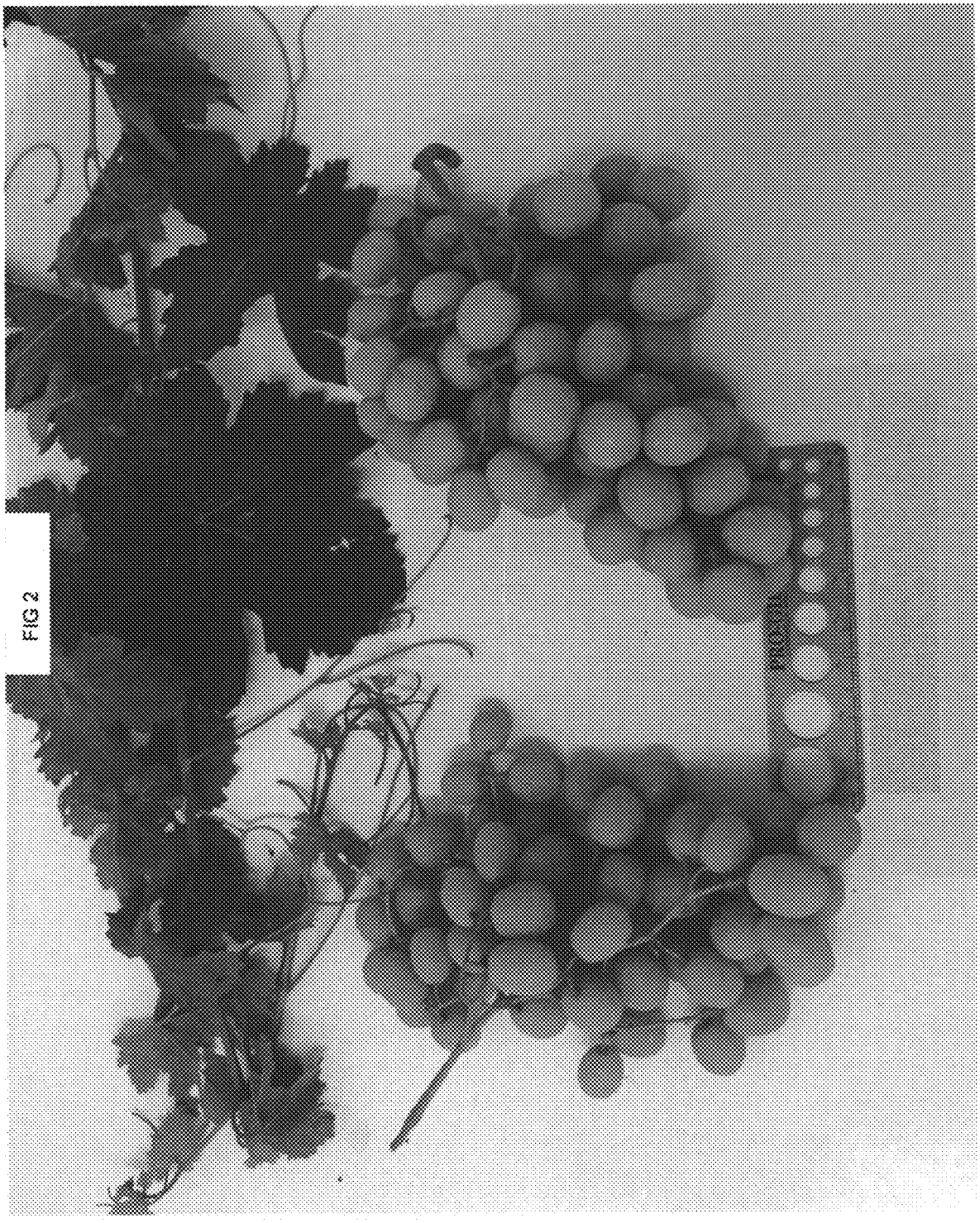
FIG. 2 Fruit clusters, green shoots, shoot tip, leaves and tendrils. Natural fruit cluster at left and cluster from vine treated with exogenous gibberellic acid and trunk girdled at right.
Figure 3:
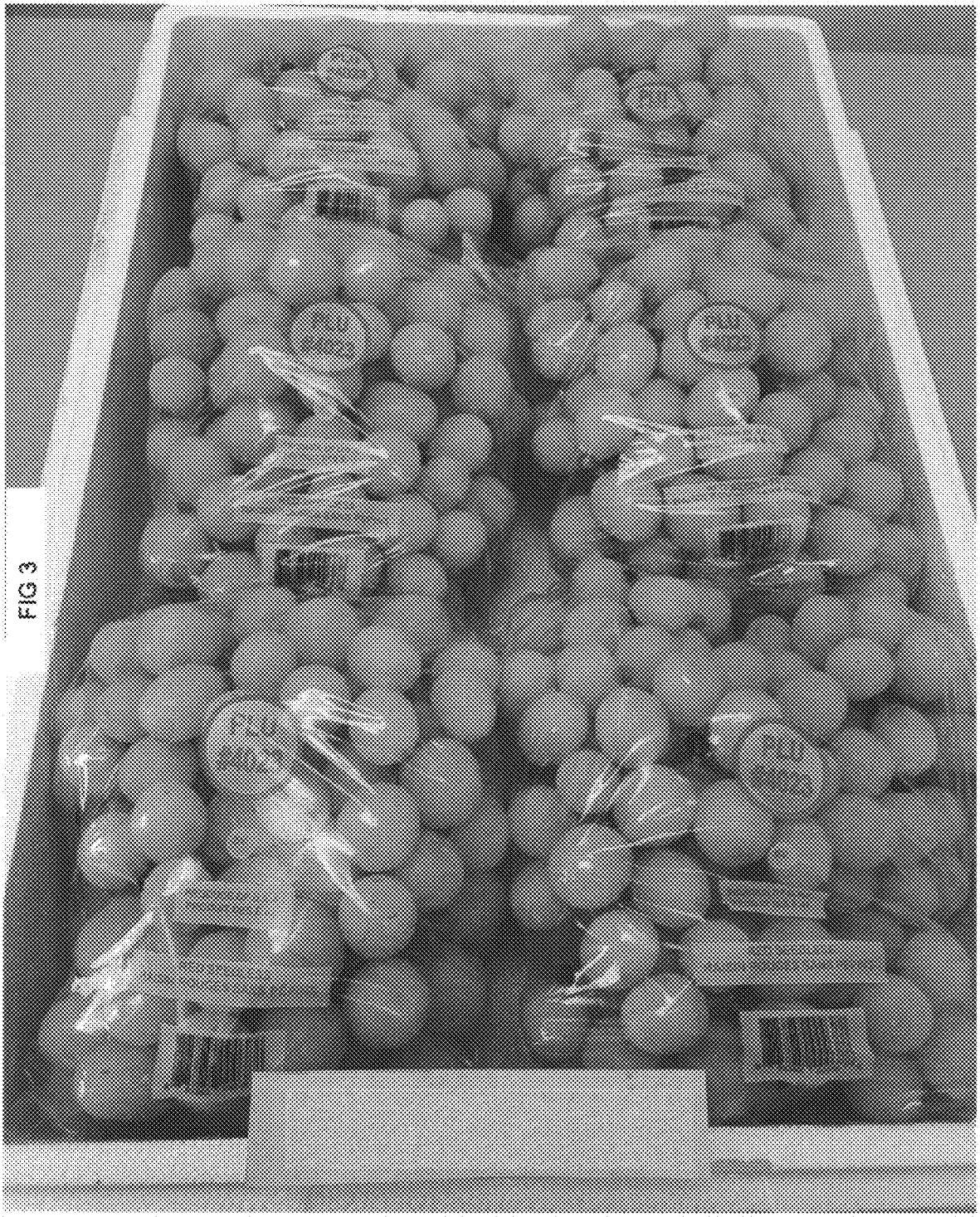
FIG. 3 Fruit clusters prepared for cold storage on day of harvest.

The following detailed description sets forth the distinctive characteristics of grapevine named 'SV34-150-338'. Descriptions of the new invention apply to vines of 'SV34-150-338' grown on 'Freedom' (unpatented) rootstock at a density of 1,537 vines per hectare grown near McFarland, Calif. in 2021. These vines were in their third year of production having been planted in 2018. These descriptions are believed to apply generally to the new variety grown under similar circumstances elsewhere. Color references are to The Royal Horticultural Society's Colour Chart, The Royal Horticultural Society, London, United Kingdom, 1966, 1986, 1995, 2001. Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in *Descriptors for Grapevine* (*Vitis spp.*) (Anonymous, International Plant Genetic Resources Institute, 1997, ISBN 92-9043-352-3).

Classification:

*Family*.—Vitaceae.
*Botanical name*.—*Vitis vinifera*.
*Variety name*.—'SV34-150-338'.

Plant:

*Vigor*.—Vigorous vines spur-pruned and shoot thinned to 32 shoots average 176 cm of growth per cane.
*Density of foliage*.—Dense.
*Productivity*.—Highly productive when spur pruned, up to 42,000 kg/hectare.
*Hardiness*.—Hardiness observed to 0° C.
*Rootstock*.—'Freedom' (unpatented).

Trunk:

*Shape*.—Broadly elliptical.
*Straps*.—Long, split.
*Surface texture*.—Shaggy.
*Trunk circumference*.—24.6 cm at 1.0 m of height.
*Inner bark color*.—RHS Greyed orange group 177B.
*Outer bark color*.—RHS Greyed orange group 177A.

Mature leaves:

*Average blade length*.—19.8 cm.
*Average blade width*.—20 cm.
*Size of blade*.—Large.
*Shape*.—Pentagonal.
*Number of lobes*.—5.
*Anthocyanin coloration of main veins on the upper side of the blade*.—Slight, only on sun exposed leaves.
*Mature leaf profile*.—Cupped upwards around entire margin.
*Blistering* (*upper surface*).—Absent.
*Leaf blade tip*.—In plane of leaf.
*Margins*.—Lobed, serrated, undulating.
*Apex*.—Broadly acuminate.
*Bases*.—Sagittate.
*Thickness*.—Medium.
*Undulation of blade between main and lateral veins*.—Slight.
*Shape of teeth*.—Broadly conical, both sides convex.
*Length of teeth*.—2-11 mm.
*Ratio length/width of teeth*.—About 1:2.
*General shape of petiole sinus*.—Variable, half open to closed.
*Tooth at petiole sinus*.—Absent.
*Petiole sinus limited by veins*.—Absent.
*Shape of upper lateral sinus*.—Closed.
*Prostrate hairs between veins* (*lower surface*).—Absent.
*Erect hairs between veins* (*lower surface*).—Absent.
*Prostrate hairs on main veins* (*lower surface*).—Sparse.
*Density of erect hairs on main veins* (*lower surface*).—Moderately sparse, limited to junctions of main veins.
*Prostrate hairs on main veins* (*upper surface*).—Sparse.
*Upper surface*.—Summer color: RHS Green group 137A. Surface texture: Smooth. Surface appearance: Smooth. Goffering of blade: Absent.
*Lower surface*.—Summer color: RHS Yellow green group 147B. Anthocyanin coloration of main veins on lower leaf surface: Present near bases of main veins, RHS Red purple group 59B. Anthocyanin coloration on laterals: Absent. Glossiness: Low. Pubescence distal portion of surface: Absent. Surface texture: Rough. Surface appearance: Dull.
*Petiole*.—Length: 14.6 cm. Length of petiole compared to middle vein: Much shorter. Density of prostrate hairs: Absent. Density of erect hairs: Absent. Color: In shade: RHS Yellow green group 144A. In sun: RHS Red purple group 59B.

Tendrils:

*Number*.—Bifurcated and trifurcated; forming at alternating nodes above node 6.
*Length*.—27.5 cm.
*Diameter at base*.—4 mm.
*Texture*.—Smooth.
*Color*.—RHS Yellow green group N144A and RHS Red purple group 59B.

Growing tips (young shoot):

*Pubescence*.—Abundant, prostrate.
*Color*.—RHS 144C (yellow green group).
*Anthocyanins*.—Absent.
*Shape*.—Rounded.
*Apex*.—Fully open.
*Shoot attitude*.—Semi-erect.

Green summer shoots:

*Shoot attitude*.—Erect.
*Internode color upper surface*.—RHS Red purple group 61A and RHS Yellow green group 144B.
*Internode color lower surface*.—RHS Red purple group 61A and RHS Yellow green group 144B.
*Node color upper surface*.—RHS Red purple group 61A.
*Node color lower surface*.—Red purple group 61A and Yellow green group 144B.
*Density of erect hairs on internodes*.—Absent.

Woody shoot:

*Canes*.—Shape, cross section: Elliptic. Internode length: 9.9 cm. Width at node: 5.8 mm. Surface: Smooth. Main color: RHS Greyed orange group 165B. Lenticels: Inconspicuous.

*Buds*.—Shape: Slightly rounded to pointed. Cane bud fruitfulness: Fruitful from basal buds one and two. Length: 7 mm. Width: 4 mm. Height: 4 mm. Color: RHS Greyed orange group 174A. Texture: Smooth. Bud burst: Medium.

Flowers:

*Flower sex*.—Perfect.

*Position of first flowering nodes*.—Usually the fourth.

*Number of inflorescences per shoot*.—1 or 2.

*Calyptra color*.—RHS Yellow Green Group 144A.

*Ovary length*.—2 mm.

*Ovary width*.—2 mm.

*Ovary color*.—RHS Yellow Green Group 144A.

*Filament length*.—2 mm.

*Filament color*.—Translucent, absence of pigmentation.

*Anther length*.—1 mm.

*Anther color*.—RHS Yellow Group 8B.

*Date of full bloom*.—May 10, 2021.

*Pollen*.—Abundant, RHS Yellow Group 8B.

Fruit:

*Ripening period*.—Late mid-season near McFarland, Calif.

*Date of ripening*.—August 30$^{th}$, near McFarland, Calif.

*Use*.—Fresh market.

*Keeping quality*.—Very good.

*Shipping quality*.—Good.

*Date of first harvest*.—September 15$^{th}$ near McFarland, Calif.

*Solids-sugar*.—High, about 20.5 brix at full maturity.

*Bunch*.—Size: Large. Length (peduncle excluded): About 24 cm. Width: About 17 cm. Weight: Natural, without gibberellic acid treatment: 1,190 g. With gibberellic acid treatment: 1630 g. Density: Well filled. Number of berries: 137. Form: Conical.

*Peduncle*.—Length: About 5 cm. Lignification: 5 mm of peduncle. Color: Non-lignified: RHS Yellow green group 144A. Lignified: RHS Greyed orange group 166C.

*Berry*.—Size: Large. Uniformity of size: Uniform. Weight Natural, without gibberellic acid treatment: 8.7 g. With gibberellic acid treatment: 11.1 g. Shape: Natural, without gibberellic acid treatment: Elliptic. With gibberellic acid treatment: Elliptic. Dimensions of Berry: Natural, without gibberellic acid treatment: Length: 2.5 cm. Width: 2.2 cm. With gibberellic acid treatment: Length: 3.3 cm. Width: 2.5 cm. Presence of seeds: Seedless; most berries develop one or two small, soft rudimentary seeds less than 3.0 mm in length. Cross section: Circular. Dimensions: Natural: Longitudinal axis: About 2.5 cm at base. Horizontal axis: About 2.2 cm. Treated with gibberellic acid: Longitudinal axis: 3.3 cm at base. Horizontal axis: About 2.5 cm. Skin color (without bloom): RHS Yellow green group N144B. Coloration of flesh: Translucent, RHS Yellow green group 145A. Juiciness of flesh: Very juicy. Berry firmness: Firm to crisp. Particular flavor: Neutral, typical *vinifera*. Bloom (cuticular wax): Medium. Pedicel length: 1.0 cm. Berry separation from pedicel: With difficulty, vascular brush well-developed.

*Skin*.—Thickness: Medium. Texture: Crisp. Reticulation: Absent. Roughness: Absent. Tenacity: Tenacious to flesh.

*Tendency to crack*.—Resistant.

Disease and insect resistance: No particular resistance or susceptibility has been observed. Normal disease control practices can be used.

Having thus described and illustrated our new variety of grapevine, we claim:

1. A new and distinct variety of grapevine plant named 'SV34-150-338', substantially as illustrated and described herein.

* * * * *